US012582454B2

(12) United States Patent
Wald et al.

(10) Patent No.: US 12,582,454 B2
(45) Date of Patent: Mar. 24, 2026

(54) BONE PLATE IMPLANTATION ASSEMBLY

(71) Applicant: KLS Martin, LP, Jacksonville, FL (US)

(72) Inventors: Bridgette Wald, Jacksonville, FL (US); Bennie W. Gladdish, Jr., Jacksonville, FL (US); Adam Grabow, Jacksonville, FL (US)

(73) Assignee: KLS MARTIN, LP, Jacksonville, FL (US)

( * ) Notice: Subject to any disclaimer, the term of this patent is extended or adjusted under 35 U.S.C. 154(b) by 266 days.

(21) Appl. No.: 18/141,332

(22) Filed: Apr. 28, 2023

(65) Prior Publication Data

US 2023/0346438 A1 Nov. 2, 2023

Related U.S. Application Data

(60) Provisional application No. 63/337,065, filed on Apr. 30, 2022.

(51) Int. Cl.
| | |
|---|---|
| *A61B 17/80* | (2006.01) |
| *A61B 17/17* | (2006.01) |
| *A61B 17/86* | (2006.01) |

(52) U.S. Cl.
CPC ........ *A61B 17/808* (2013.01); *A61B 17/1728* (2013.01); *A61B 17/8085* (2013.01); *A61B 17/865* (2013.01); *A61B 17/8057* (2013.01)

(58) Field of Classification Search
CPC .. A61B 17/808; A61B 17/1728; A61B 17/865
See application file for complete search history.

(56) References Cited

U.S. PATENT DOCUMENTS

| | | | | |
|---|---|---|---|---|
| 7,588,576 B2 * | 9/2009 | Teague | .................. | A61F 2/2875 |
| | | | | 606/280 |
| 8,414,594 B2 * | 4/2013 | Berger | .................. | A61B 50/30 |
| | | | | 606/104 |
| 9,271,732 B2 * | 3/2016 | Walker | .................. | A61B 17/10 |
| 9,572,611 B2 * | 2/2017 | Wand | ................. | A61B 17/1728 |
| 10,226,290 B2 * | 3/2019 | Steffensmeier | .... | A61B 17/1728 |
| 11,033,284 B2 * | 6/2021 | Tsai | .................. | A61B 17/8076 |
| 2020/0337751 A1 * | 10/2020 | Detweiler | .......... | A61B 17/8038 |
| 2021/0267650 A1 * | 9/2021 | Didyk | .................. | A61B 50/20 |
| 2023/0301693 A1 * | 9/2023 | Garcia | ................. | A61B 17/808 |

* cited by examiner

*Primary Examiner* — David W Bates
(74) *Attorney, Agent, or Firm* — Thomas C. Saitta

(57) ABSTRACT

A bone plate implantation assembly having a plate holder composed of an elastomeric polymer, a bone plate and bone screws, the plate holder having a compressible midface retention protrusion located within a plate-receiving recess and the bone plate having a midbody retention aperture whereby the bone plate is temporarily retained on the plate holder by inserting the midface retention protrusion into the midbody retention aperture.

14 Claims, 4 Drawing Sheets

BONE PLATE IMPLANTATION ASSEMBLY

BACKGROUND OF THE INVENTION

This invention relates generally to the field of systems and assemblies for the implantation of bone plates of the type used to connect adjacent bone segments or cover openings in a bone, which include handheld screw guides devices structured to temporarily retain one or more screws or similar mechanical fasteners in fixed locations and orientations, the locations aligning with screw-receiving apertures in a plate or similar member to be affixed to a bone, wherein the screws are driven from the screw-retaining guide through the screw-receiving apertures of the plate and into the bone to secure and affix the plate to the bone. The screw-retaining devices are often referred to as screw guides, caddies or magazines. More particularly, the invention relates to such systems or assemblies wherein the screw-retaining guide further serves as a bone plate holder which temporarily retains the bone plate in an assembled unit, and even more particularly wherein the main body of the screw-retaining guide and holder is composed of a flexible, compressible, elastomeric material.

It is common in the medical field to require affixation of a substantially rigid, malleable or even slightly flexible bone plate to a bone or separate bone segments, such as for example a sternal plate affixed to longitudinally divided sternal halves or a cranial plate positioned across a cranial opening, using mechanical fasteners, i.e., bone screws. The bone plates have multiple screw-receiving apertures, threaded or non-threaded, through which bone screws are driven into the underlying bone. To speed up the process of affixing the bone plate and to ensure that the bone screws are driven into the bone at the proper angle, it is known to provide handheld screw-retaining guide devices having bores positioned to match the locations of the screw-receiving apertures in the bone plate. The bone screws are temporarily disposed within bores provided in the screw guide, i.e., pre-loaded. The screw guide is then aligned with or temporarily mounted onto the bone plate, thereby properly locating all the bone screws with their respective screw-receiving apertures, with the screws then being driven from the screw guide, through the bone plate and into the underlying bone once the bone plate is properly positioned on the bone. In an improved design, the screw guide also functions as a temporary holder of the bone plate, thereby enabling the surgeon to position the bone plate at the desired location on the bone by holding the combination screw guide and plate holder.

The temporary retention of the bone plate on the combination screw guide and plate holder may be accomplished in various manner, such as through clips, a friction or compressive fit, mechanical interlocking or by providing a recess in the screw guide to receive the bone plate. U.S. Pat. No. 7,588,576 discloses an assembly wherein a cylindrical guide/holder composed of an elastomeric material is provided with circumferentially spaced screw-receiving bores, the bores being aligned with screw-receiving apertures in a disk-shaped bone plate. The bone plate is temporarily retained by a ring of compressible, elastic protrusions which are forced into correspondingly spaced and sized mounting apertures present on the bone plate. U.S. Pat. No. 9,572,611 illustrates another such assembly, wherein the bone plate is temporarily retained on the elastomeric screw guide/holder by, for example, providing a recess on abutting side of the guide/holder that matches the configuration of the bone plate, but is slightly smaller, such that the bone plate is retained by pressing it into the recess. A problem encountered in these devices is that in many circumstances it is necessary for the surgeon to bend the bone plate prior to affixation so that is better conforms to the surface configuration or geometry of the bone. Since the bone plate is retained on the abutting surface of the guide/holder by physical structures (protrusions, recess walls) positioned near or at the edges of the bone plate, bending of the bone plate often results in the inability of the combination screw guide and plate holder to retain the bone plate.

To address this problem, more complicated structural designs for the combination screw guide and plate holder have been proposed, such as for example as shown in U.S. Pat. Nos. 10,226,290 and 11,033,284 and in U.S. Patent Publ. No. 2021/0267650. The proposed solutions typically utilize clips or other mechanical connectors to join the bone plate to the combination screw guide and plate holder, which result in unwieldy devices which require complicated manufacturing.

It is an object of this invention to provide a flexible screw guide and bone plate holder affixation system or assembly that improves over known systems by providing the combination screw guide and plate holder as a uniform body composed of a flexible, elastomeric, compressible material with no added internal or external structural support members, the combination screw guide and plate holder provided in combination with a bone plate which is temporarily connected to or retained by the combination screw guide and plate holder, wherein the combination screw guide and plate holder is provided with a centrally located mid-body retention protrusion which temporarily mates with a centrally located mid-body mounting aperture disposed on the bone plate. The centralized mid-body location allows the bone plate to remain joined to the screw combination screw guide and plate holder even when the periphery or extensions arms of the bone plate have been bent as required for proper fit onto the bone surface. Such a combination screw guide and plate holder is easily handled by the surgeon, reduces manufacturing costs and requires no assembly of components.

SUMMARY OF THE INVENTION

The invention in summary is a bone plate implantation system or assembly comprising the combination of a flexible screw guide and bone plate holder uniformly composed of an elastomeric polymer or copolymer, a bone plate structured and configured for affixation to a bone, and bone screws. The flexible screw guide and bone plate holder is provided with bores which receive and temporarily retain the bone screws, the screw-retaining bores extending completely through the body of the flexible screw guide and bone plate holder into a plate-receiving recess disposed on the distal surface. A centralized midface retention protrusion is positioned within the plate-receiving recess.

The bone plate is a thin, structurally rigid member comprising screw-receiving apertures and a centralized midbody retention aperture. The configuration of the peripheral edge of the bone plate and the configuration of the plate-receiving recess are corresponding, with the overall lateral dimensions of the bone plate around the peripheral edge preferably being slightly larger than the overall lateral dimensions of the plate-receiving recess. Preferably, the configuration of the centralized midface retention protrusion of the flexible screw guide and bone plate holder and the centralized midbody retention aperture of the bone plate are corresponding, with the lateral dimensions of the centralized midface retention protrusion being slightly larger than the lateral dimensions of the centralized midbody retention aperture However the configuration or the midface retention protrusion may differ from that of the midbody retention aperture provided that there is a sufficient portion of the. In this manner, the bone plate is temporarily mounted onto or joined to the flexible screw guide and bone plate holder by pressing the bone plate into the plate-receiving recess such that the midbody centralized retention aperture is compressively retained by the midface centralized retention protrusion and, preferably, the peripheral edge of the bone plate is compressively retained by the elastomeric properties of the recess wall.

The matching configurations of the plate-receiving recess and the bone plate ensure proper alignment between the screw-retaining bores of the flexible screw guide and bone plate holder and the screw-receiving apertures of the bone plate, such that with the bone plate properly positioned on the bone, the bone screws can be driven through the screw-retaining bores and the screw-receiving apertures and then into the bone. With the bone plate secured to the bone, the flexible screw guide and bone plate holder is easily removed from the bone plate.

The key advantage of the assembly as described over the prior art devices is the provision of the centralized midface retention protrusion and centralized midbody retention aperture as the primary means for temporarily retaining the bone plate on the flexible screw guide and bone plate holder. In many circumstances the bone plate will need to be adjusted by the surgeon to better conform to the surface of the bone, which is done by removing the bone plate from the assembly and bending some or all of the outer portions or extensions of the bone plate. In prior art systems, the bending of the bone plate renders the guide/holder inoperable or less effective, since the bent portions of the bone plate can no longer connect or align with retention means of the guide/holder. This problem is overcome by primarily securing the bone plate to the flexible screw guide and bone plate holder at or near the center or midbody rather than at or near the peripheral edge, since the central area is not adversely affected by reshaping the outer portions of the bone plate.

DETAILED DESCRIPTION OF THE INVENTION

The invention will now be described in detail with reference to the drawings, which are intended to be representative and illustrative and not limiting in scope. The term "flexible" is used herein to encompass a material that has elastomeric properties, in that it is compressible yet will return to its original configuration once the compressive bias is removed. To improve readability, the term "plate holder" is used herein as a shorthand substitute for the expanded term "flexible screw guide and bone plate holder", such that use of the former equates to use of the latter. The term "distal" is used herein to designate the direction toward to the bone when the assembly is positioned on the bone in use, such that the distal face of the plate holder is the side retaining the bone plate when assembled. The term "lateral" is used herein to designate the transverse direction generally perpendicular to the distal direction.

Figure 1:
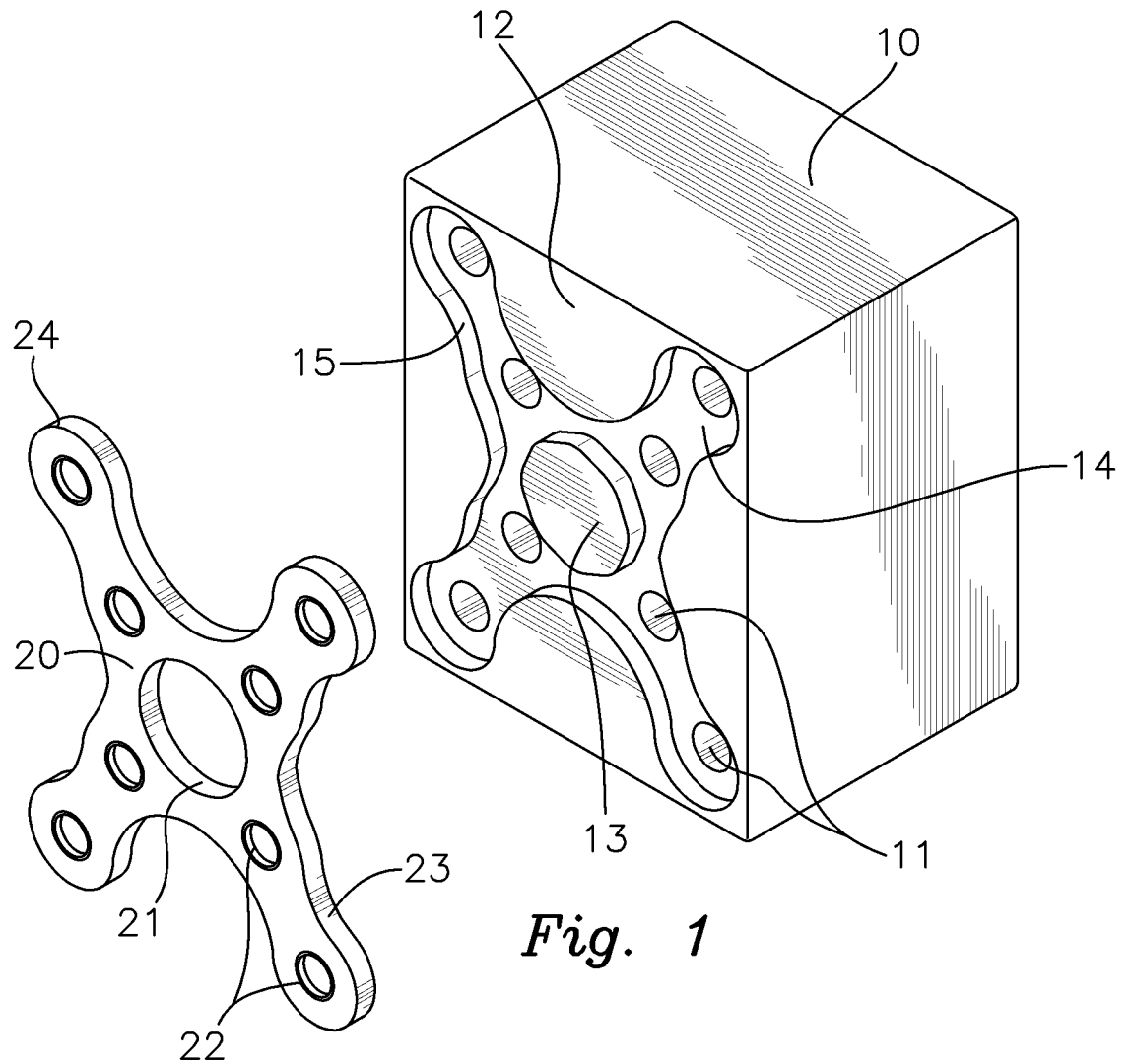
FIG. 1 illustrates an exploded perspective view of an embodiment of the invention wherein the configuration of the bone plate is generally X-shaped.
Figure 2:
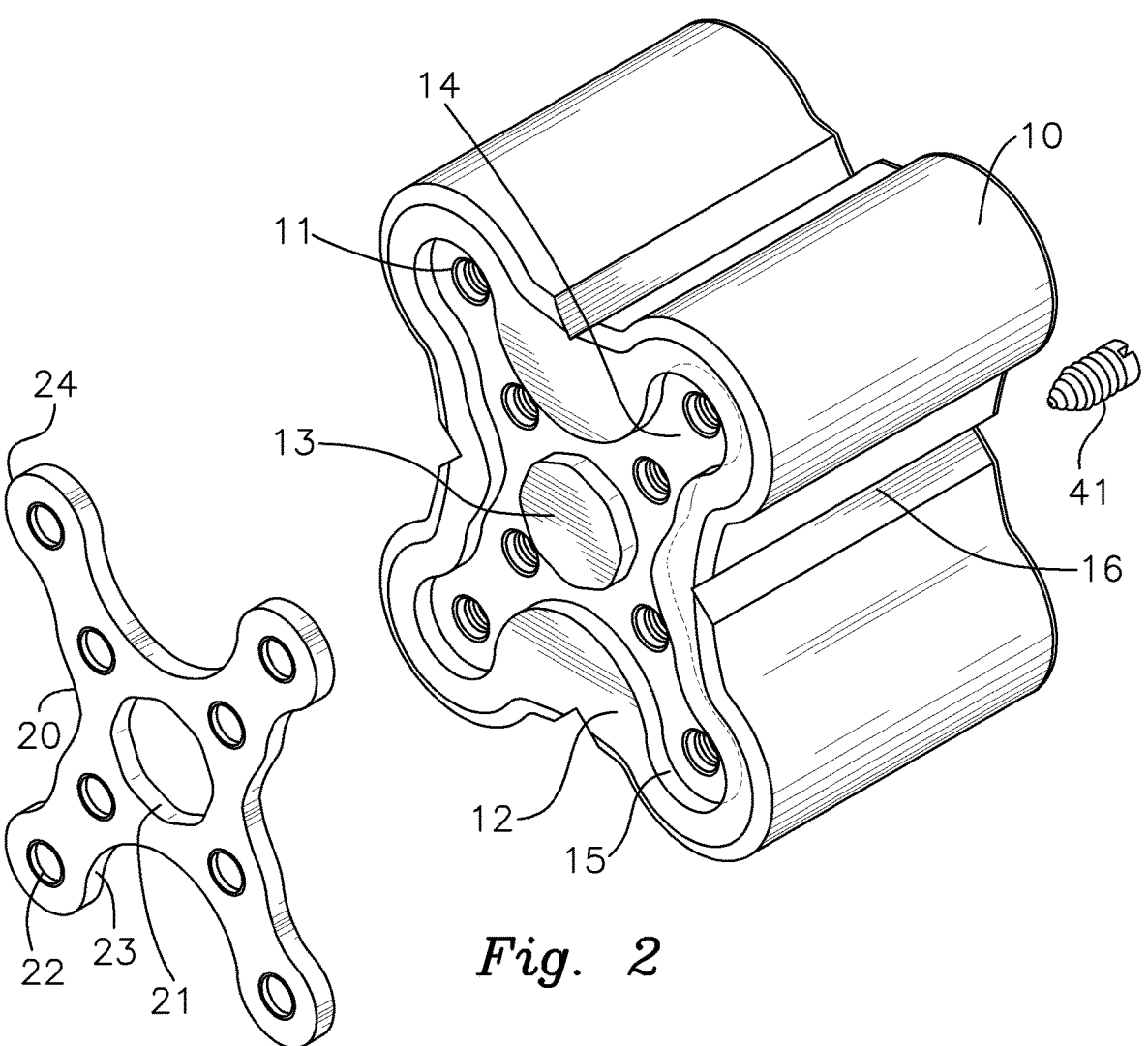
FIG. 2 illustrates an exploded perspective view of an alternate embodiment of the invention wherein the flexible screw guide and bone plate holder is configured to mimic the configuration of the X-shaped bone plate.

A basic embodiment of the assembly or system described herein is illustrated in FIG. 1, while a more ergonomic configuration of the plate holder 10 is illustrated in FIG. 2. The invention in general terms is an assembly, system or combination of a plate holder 10, a bone plate 20 and bone screws 41. The bone plate 20 is temporarily mounted on or retained by the plate holder 10 by compressive or biased elastomeric properties, such that the bone plate 20 is retained on the plate holder 10 during movement and positioning, yet the plate holder 10 is easily removed from the bone plate 20 by hand strength once the bone plate 20 is affixed to the bone.

Figure 3:
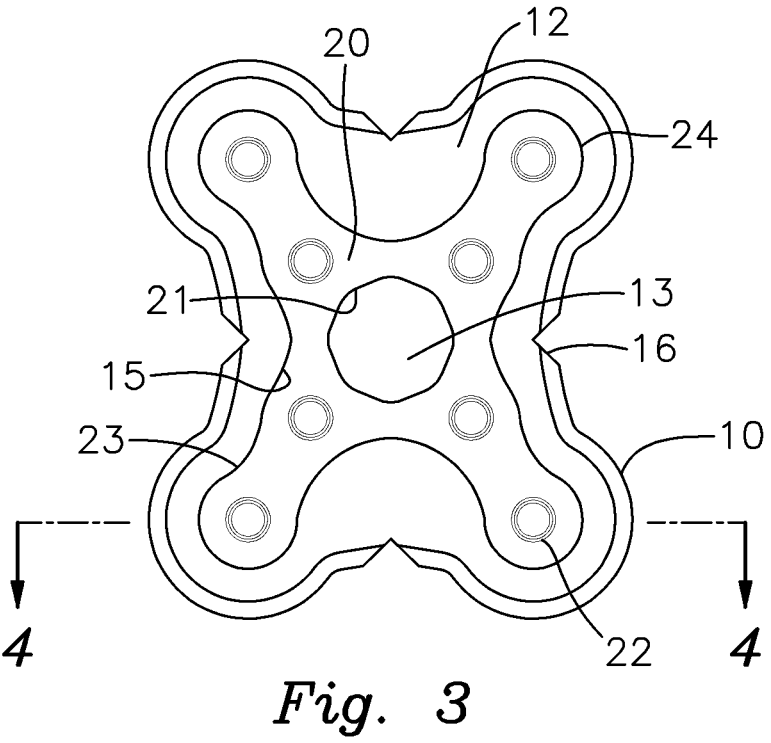
FIG. 3 illustrates a distal view of the embodiment of FIG. 2.
Figure 5:
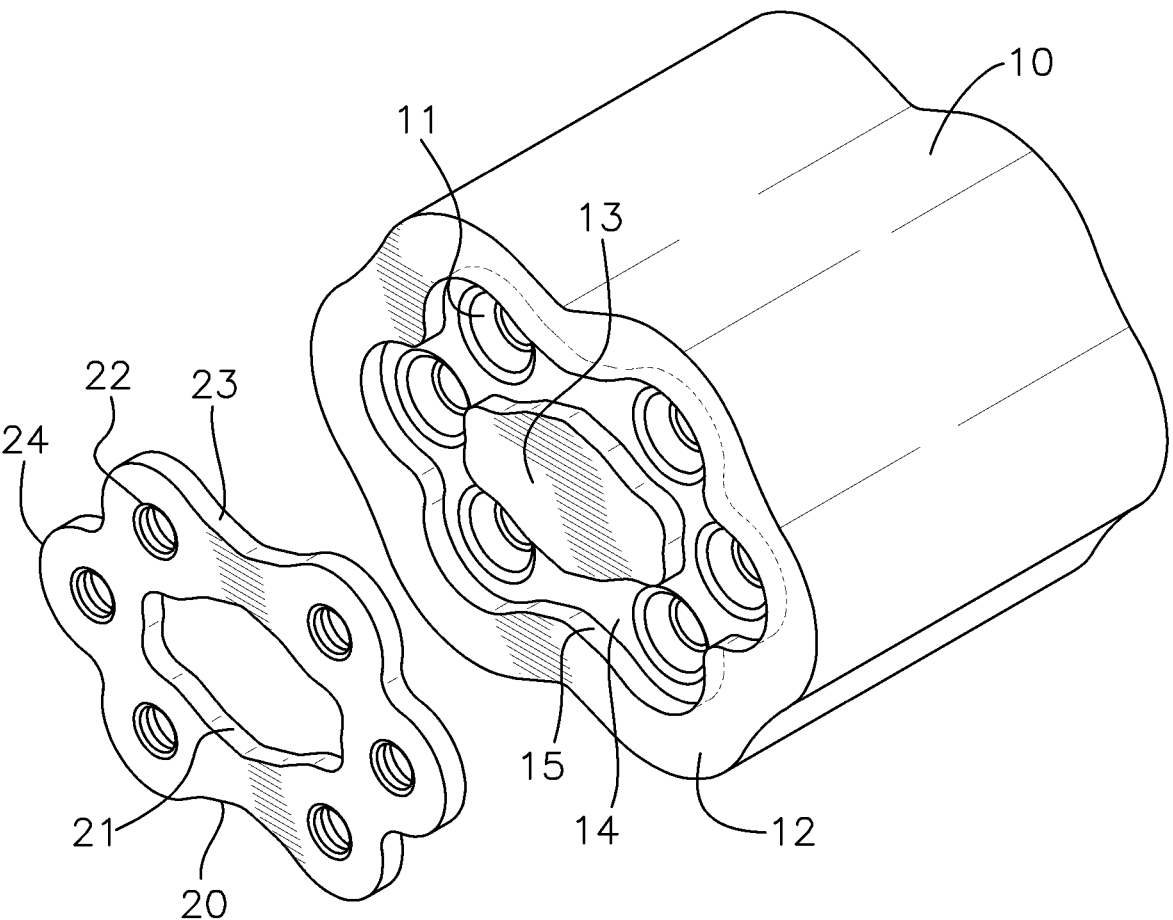
FIG. 5 illustrates an exploded perspective view of another alternate embodiment of the invention wherein the flexible screw guide and bone plate holder is configured to mimic the configuration of the generally oval bone plate.

Bone plates 20 are well known in the art. Such implants are used to join broken or separated bone segments, such as for example a severed sternum, in a relatively rigid, fixed relationship to allow for healing and mechanical support, and also to cover gaps or holes in a bone, such as for example a cranial bore. The bone plates 20 are provided with screw-receiving apertures 22 such that bone screws 41 may be inserted through the screw-receiving apertures 22 and into the bone to secure the bone plate 20 to the bone. The bone plates 20 are composed of a biocompatible material of suitable strength properties, such as titanium, ceramics or the like. The bone plates 20 are typically thin in depth with the peripheral edge 23 defining the configuration or shape of the bone plate 20. Typical bone plates 20 can be substantially or generally rectangular, circular, oval (FIG. 5) or X-shaped (FIGS. 1-3), such that the configurations may define extensions 24, which may comprise extended body portions or arms. The bone plates 20 may be malleable such that the extensions 24 or the overall bone plate 20 may be bent prior to affixation to the bone to better approximate or match the surface configuration of the bone.

The bone plates 20 of this invention are provided with a centralized midbody retention opening 21 which is of significantly greater size than the screw-receiving apertures 22. The shape of the midbody retention opening 21 may vary, although a non-circular midbody retention opening 21 is preferred to better ensure proper alignment and orientation of the bone plate 20 on the plate holder 10. For symmetrical bone plates 20 that possess a true center, the center of the midbody retention opening 21 is preferably aligned with the true center. For other bone plate 20 configurations, a suitable midbody location is determined such that bending or any bone plate extensions 24 will not negatively impact retention of the bone plate 20 by the plate holder 10.

The plate holder 10 is a uniform body composed of an elastomeric polymer or copolymer, such as for example a silicone, whereby the plate holder 10 is flexible, compressible and retains a neutral shape when any compressive or biasing forces are removed. The polymer should by cleared for use for patient contact or implantability and preferably has a Shore A Hardness range from approximately 40-100 and/or a Shore D Hardness range from approximately 10-90. Most preferably, the Shore A Hardness range is approximately 70-90. No internal or external bracing or strengthening members or components are required.

The overall configuration or shape of the plate holder 10 may vary. In a basic embodiment, the plate holder may be block-shaped (FIG. 1), but preferably the shape of the plate holder 10 better approximates the configuration of the bone plate 20 (FIGS. 2, 3, 5), as this provides better visualization for the surgeon as to the location of the bone plate 20 during insertion and affixation to the bone. The matching configurations of the bone plate 20 and the plate holder 10 may also provide a more ergonomic or comfortable grip for the surgeon. The plate holder 10 may be provided with alignment indicators 16 or other indicia.

Figure 4:
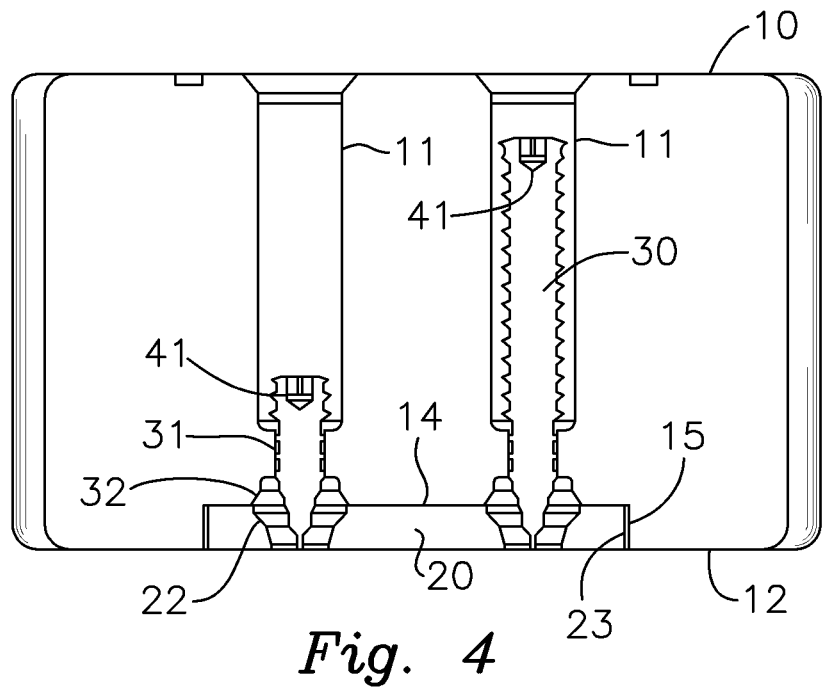
FIG. 4 illustrates a partially exposed side view taken along line 4-4 of the embodiment of FIG. 2 showing the screw-retaining bores of the flexible screw guide and bone plate holder and the screw-receiving apertures of the bone plate.

The plate holder 10 is provided with screw-retaining bores 11 configured to temporarily retain bone screws 41. The number and location of the screw-retaining bores 11 correspond to the number and location of the screw-receiving apertures 22 in the bone plate 20. The screw-retaining bores 11 extend completely through the plate holder 10, opening into a plate-receiving recess 14 positioned in the distal surface 12 of the plate holder 10. The screw-retaining bores 11 may have a simple tubular structure, but preferably are provided with screw-retention structures 30, such as annular or longitudinal ribs which retain and properly orient the bone screws 41 while allowing the bone screws 41 to be easily driven from the screw-retaining bores 11, through the screw-receiving apertures 22 of the attached bone plate 20 and into the bone. A suitable configuration is shown in FIG. 4, wherein the screw-retaining bores 11 comprise ridged screw retention structures 30, a narrowed alignment neck 31 and flared distal openings 32. The screw-retaining bore 11 on the right is shown retaining a relatively short bone screw 41, while the screw-retaining bore 11 on the left retains a much longer bone screw 41. The flared distal openings 32, in combination with the inherent flexibility of the plate holder 10, allow for insertion of the bone screws 41 into the bone plate 20 at angles of up to approximately 20 degrees from perpendicular when the extensions 24 have been bent to better conform to the bone surface.

The plate holder 10 is provided with a plate-receiving recess 14 which is disposed on the distal surface 12 of the plate holder 10. The plate-receiving recess 14 has a recess wall 15 and is configured to correspond or match the configuration of the bone plate 20, i.e., the configuration or shape of the recess wall 15 of the plate-receiving recess 14 corresponds or matches the configuration or shape of the peripheral edge 23 of the bone plate 20. This ensures that the screw-retaining bores 11 of the plate holder 10 are properly aligned with the screw-receiving apertures of the bone plate 20 when the bone plate 20 is mated with the plate holder 10. Most preferably, the lateral dimensions of the plate-receiving recess 14 are slightly smaller than the lateral dimensions of the peripheral edge 23 of the bone plate 20, such that insertion of the bone plate 20 into the plate-receiving recess 14 outwardly biases or compresses the recess wall 15, thereby providing temporary retention of the bone plate 20 by the plate holder 10. To insure proper initial contact between the bone plate 20 and the bone upon implantation, the depth of the plate-receiving recess 14 is most preferably equal to or less than the depth of the bone plate 20.

The plate holder 10 is also provided with a centralized, compressible, midface retention protrusion 13, which is located within the plate-receiving recess 14. The midface retention protrusion 13 is located and configured to correspond to the location and configuration of the midbody retention aperture 21 of the bone plate 20 when the bone plate 20 is mounted to the plate holder 10. The lateral dimensions of the midface retention protrusion 13 are slightly greater than the lateral dimensions of the midbody retention aperture 21, whereby insertion of the bone plate 20 into the plate-receiving recess 14 of the plate holder 10 inwardly biases or compresses the midface retention protrusion 13, thereby providing temporary retention of the bone plate 20 by the plate holder 10. Preferably the overall peripheral configuration of the midface retention protrusion 13 generally corresponds or matches the overall configuration of the midbody retention aperture 22 of the bone plate 20. However, the configuration or the midface retention protrusion 13 may differ from that of the midbody retention aperture 22 provided that there is a sufficient portion of the midface retention protrusion 13 compressed to retain the bone plate 20 on the plate holder 10. For example, the midbody retention aperture 22 of the bone plate 20 could be rectangular while the midface retention protrusion 13 could be formed in the shape of a cross of slightly greater dimensions. The midface retention protrusion 13, as well as other portions of the plate holder 10, may be provided with one or more interior bores or passages in order to reduce the amount of material and/or increase flexibility.

For use, the bone screws 41 are inserted into the screw-retaining bores 11 of the plate holder 10 and the bone plate 20 is mounted into the plate-receiving recess 14 of the plate holder 10, the midbody retention aperture 21 of the bone plate 20 compressing or biasing the elastomeric midface retention protrusion 13 located in the plate-receiving recess 14, such that the bone plate 20 is temporarily retained by the plate holder 10. This combination defines the bone plate implantation assembly. The surgeon then grasps the plate holder 10 and positions the bone plate 20 at the desired location on the bone. The bone screws 41 are then driven through and out of the screw-retaining bores 11, through the screw-receiving apertures 22 of the bone plate 20 and into the bone. Once the bone plate 20 is affixed to the bone, the surgeon pulls the plate holder 10 free from the bone plate 20.

In the event that the bone plate 20 needs to be bent or otherwise adjusted to better conform to the bone surface configuration, the bone plate 20 is pulled from the plate holder 10 and the surgeon adjusts the bone plate 20 by bending, angling or otherwise shaping the extensions 24 of the bone plate 20, which may result in one or all of the extensions 24 no longer mating with or fitting into the plate-receiving recess 14. The structure of the plate holder 10 and the bone plate 20, specifically the presence of the midface retention protrusion 13 and the midbody retention aperture 22, allows the bone plate 20 to be reattached to the plate holder 10 solely by the compression or biased fit between the midface retention protrusion 13 and the midbody retention aperture 22. The affixation procedure is then carried on as described.

Dependent upon the flexibility, elasticity and thickness of the plate holder 10, the configuration of the bone plate 20 and the plate holder 10, the location of the screw-receiving apertures 22, the dimensions and extent of the extensions 24, the length of the bone screws 41, and other variables, it is likely that bending the bone plate extensions more than approximately 20 degrees out of plane will preclude the use of the screw-retaining bores 11 in the outermost or highly bent portions for affixing the bone plate 20 to the bone, since the angle between the axes of the screw-retaining bores 11 relative to the axes of the screw-receiving apertures 22 in the bone plate 20 will become too great. In such case, the adjusted bone plate 20 is remounted onto the plate holder 10 utilizing the combination of the midface retention protrusion 13 and the midbody retention aperture 22. The bone plate 20 is then properly positioned and affixed to the bone using the bone screws 41 retained in at least one of the remaining functional screw-retaining bores 11, i.e., the innermost or most planar areas relative to the bone plate 20, which remains in alignment with at least one of the screw-receiving apertures 22. The plate holder 10 is then separated from the bone plate 10 and bone screws 41 are inserted and driven directly through the remaining screw-receiving apertures 22 and into the bone.

Alternatively, the screw-receiving bores 11 may be used as drill guides to drill pilot holes for the bone screws 41 in the bone. With the bone screws 41 removed from the plate holder 10 and the bone plate 20, mounted on the plate holder 10, properly situated against the bone, the surgeon inserts a drill bit into the empty screw-receiving bores 11 and drills the pilot holes. The bone screws 41 are then inserted, or reinserted, into the screw-receiving bores 11 and the affixation procedure is carried on as described.

It is contemplated that equivalents and substitutions for certain elements and structures described above may be obvious to those of skill in the art, and therefore the true scope and definition of the invention is to be as set following claims.

We claim:

1. A bone plate implantation assembly comprising:

a bone plate comprising, a midbody retention aperture, screw-receiving apertures, an outer peripheral edge and extensions;

bone screws; and a plate holder composed of an elastomeric polymer or copolymer, a compressible midface retention protrusion, screw-retaining bores, a distal surface, and a plate-receiving recess disposed in the distal surface of the plate holder and having a recess wall configured to receive the outer peripheral edge of the bone plate;

wherein the bone screws are temporarily retained within the screw-retaining bores, the screw-retaining bores are aligned with the screw-receiving apertures, and the bone plate is temporarily positioned within the plate-receiving recess; and wherein with the midbody retention aperture mounted onto the compressible midface retention protrusion the bone plate is removably retained by the plate holder, and wherein the combination of the compressible midface retention protrusion and the midbody retention aperture alone is sufficient to removably retain the bone plate on the plate holder.

2. The bone plate implantation assembly of claim 1, such that with one or more of the extensions bent away from the plate holder and out of the plate-receiving recess, the bone plate is removably retained on the plate holder by the combination of the midface retention protrusion and the midbody retention aperture.

3. The bone plate implantation assembly of claim 1, wherein the recess wall is compressible such that the recess wall is compressed by the peripheral edge of the bone plate when the bone plate is removably mounted onto the plate holder.

4. The bone plate implantation assembly of claim 3, such that with one or more of the extensions bent away from the plate holder and out of the plate-receiving recess, the bone plate is removably retained on the plate holder by the combination of the midface retention protrusion and the midbody retention aperture.

5. The bone plate implantation assembly of claim 1, wherein the plate holder is composed of a single elastomeric polymer or copolymer.

6. The bone plate implantation assembly of claim 5, wherein the elastomeric polymer or copolymer possesses a Shore A Hardness range from approximately 40-100 and/or a Shore D Hardness range from approximately 10-90.

7. The bone plate implantation assembly of claim 5, wherein the elastomeric polymer or copolymer possesses a Shore A Hardness range of approximately 70-90.

8. The bone plate implantation assembly of claim 1, wherein the extensions of said bone plate are arms extending outwardly from the midbody retention aperture.

9. The bone plate implantation assembly of claim 1, wherein the extensions of said bone plate are body portions extending outwardly from the midbody retention aperture.

10. The bone plate implantation assembly of claim 1, wherein the plate holder has a shape corresponding to the peripheral edge of the bone plate.

11. The bone plate implantation assembly of claim 1, wherein the plate holder is composed of silicone.

12. The bone plate implantation assembly of claim 2, wherein at least one of the screw-retaining bores of the plate holder remains aligned with at least one of the screw-receiving apertures of the bone plate.

13. The bone plate implantation assembly of claim 1, wherein the lateral dimensions of the midface retention protrusion are slightly greater than the lateral dimensions of the midbody retention aperture.

14. The bone plate implantation assembly of claim 3, wherein the lateral dimensions of the plate-receiving recess are slightly smaller than the lateral dimensions of the peripheral edge.

* * * * *